(12) United States Patent
Hauger et al.

(10) Patent No.: US 11,953,687 B2
(45) Date of Patent: Apr. 9, 2024

(54) HEAD-MOUNTED VISUALIZATION UNIT AND VISUALIZATION SYSTEM COMPRISING LIGHT-TRANSMISSIVE OPTICAL SYSTEM

(71) Applicant: Carl Zeiss Meditec AG, Jena (DE)

(72) Inventors: Christoph Hauger, Aalen (DE); Stefan Saur, Aalen (DE); Christoph Schaeff, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 17/909,270

(22) PCT Filed: Mar. 1, 2021

(86) PCT No.: PCT/EP2021/055034
§ 371 (c)(1),
(2) Date: Sep. 2, 2022

(87) PCT Pub. No.: WO2021/175776
PCT Pub. Date: Sep. 10, 2021

(65) Prior Publication Data
US 2023/0088437 A1     Mar. 23, 2023

(30) Foreign Application Priority Data

Mar. 2, 2020 (DE) .................. 10 2020 202 624.6
Nov. 24, 2020 (DE) .................. 10 2020 131 029.3

(51) Int. Cl.
*G02B 27/01* (2006.01)
*A61B 90/00* (2016.01)
(Continued)

(52) U.S. Cl.
CPC .......... *G02B 27/0172* (2013.01); *A61B 90/37* (2016.02); *G02B 5/30* (2013.01);
(Continued)

(58) Field of Classification Search
CPC .. G02B 27/0172; G02B 5/30; G02B 27/0179; G02B 30/25; G02B 27/283;
(Continued)

(56) References Cited

U.S. PATENT DOCUMENTS 6,559,813 B1   5/2003   DeLuca et al.
6,683,726 B2   1/2004   Endo et al.
(Continued)

FOREIGN PATENT DOCUMENTS

DE   10 2017 123 894 B3   2/2019
DE   10 2018 2015 931 A1   10/2019
(Continued)

OTHER PUBLICATIONS

International Preliminary Report on Patentability, WIPO Application No. PCT/EP2021/055034, dated Jul. 4, 2022.
(Continued)

*Primary Examiner* — Que Tan Le
*Assistant Examiner* — Mai Thi Ngoc Tran
(74) *Attorney, Agent, or Firm* — ALSTON & BIRD LLP (57) ABSTRACT

A head-mounted visualization unit is provided with an at least partially light-transmissive optical system. The optical system has a first optical channel assigned to a first eye of a user and a second optical channel assigned to a second eye of the user. The first optical channel is substantially transmissive to optical radiation of a first polarization and substantially opaque to optical radiation of a second polarization, with the first polarization substantially orthogonal to the second polarization. The second optical channel is substantially transmissive to optical radiation of the second polarization and substantially opaque to optical radiation of the first polarization. A polarizer and a light attenuator are
(Continued)

arranged in the first optical channel. The light attenuator is arranged downstream of the polarizer in a direction toward the first eye of the user.

14 Claims, 7 Drawing Sheets

(51) Int. Cl.
 *G02B 5/30* (2006.01)
 *G02B 30/25* (2020.01)
 *G02B 27/28* (2006.01)
(52) U.S. Cl.
 CPC ......... *G02B 27/0179* (2013.01); *G02B 30/25* (2020.01); *A61B 2090/372* (2016.02); *G02B 2027/0118* (2013.01); *G02B 2027/0138* (2013.01); *G02B 2027/0178* (2013.01); *G02B 2027/0187* (2013.01); *G02B 27/283* (2013.01)
(58) Field of Classification Search
 CPC .... G02B 2027/0118; G02B 2027/0138; G02B 2027/0178; G02B 2027/0187; A61B 90/37; A61B 2090/372; A61B 2017/00203; A61B 2017/00216; A61B 2090/371; A61B 2090/502
 USPC ........................................................ 250/225
 See application file for complete search history.

(56) References Cited

U.S. PATENT DOCUMENTS

| | | | |
|---|---|---|---|
| 10,078,236 | B2 | 9/2018 | Hayashi et al. |
| 10,642,040 | B2 | 5/2020 | Mukawa |
| 10,659,772 | B1 | 5/2020 | Hager et al. |
| 11,150,479 | B2 | 10/2021 | Saur et al. |
| 11,670,054 | B2 | 6/2023 | Coup et al. |
| 2014/0340287 | A1 | 11/2014 | Achilefu et al. |
| 2015/0260995 | A1 | 9/2015 | Mukawa |
| 2016/0034048 | A1 | 2/2016 | Tanaka et al. |
| 2017/0184894 | A1* | 6/2017 | Hayashi .............. G02F 1/13318 |
| 2017/0244958 | A1 | 8/2017 | Shanmugam |
| 2017/0323482 | A1 | 11/2017 | Coup et al. |
| 2018/0089871 | A1 | 3/2018 | Ko et al. |
| 2018/0262743 | A1 | 9/2018 | Casas |
| 2019/0255946 | A1 | 8/2019 | Takahashi |
| 2019/0339528 | A1 | 11/2019 | Freeman et al. |
| 2020/0007857 | A1 | 1/2020 | Kasahara et al. |
| 2020/0268236 | A1 | 8/2020 | Chiba et al. |
| 2023/0087402 | A1 | 3/2023 | Hauger et al. |

FOREIGN PATENT DOCUMENTS

| | | |
|---|---|---|
| JP | H08-286141 A | 11/1996 |
| JP | 2003 250812 A | 9/2003 |
| JP | 2017-203952 A | 11/2017 |
| WO | WO 2001074235 A1 | 10/2001 |
| WO | WO 2011160200 A1 | 12/2011 |
| WO | WO 2012/039877 A1 | 3/2012 |
| WO | WO 2013/175465 A1 | 11/2013 |
| WO | WO 2015/126466 A1 | 8/2015 |
| WO | WO 2019/049997 A1 | 3/2019 |
| WO | WO 2021/175727 A1 | 9/2021 |

OTHER PUBLICATIONS

Office Action (English Translation) of German Application No. 10 2020 131 029.3, dated Jan. 9, 2021.
Offce Action of German Application No. 10 2020 131 029.3, dated Sep. 1, 2021.
Office Action (English Translation) of German Application No. 10 2020 202 624.6, dated Apr. 1, 2021.
Office Action of German Application No. 10 2020 202 624.6, dated Jan. 4, 2021.
PCT International Search Report and Written Opinion of the International Searching Authority, WIPO Application No. PCT/EP2021/054900, dated Apr. 21, 2021.
PCT International Search Report and Written Opinion of the International Searching Authority, WIPO Application No. PCT/EP2021/055034, dated May 17, 2021.
Office Action of JP Patent Application No. 2022-552670, dated Jun. 20, 2023, 8 page(s).
Office Action of JP Patent Application No. 2022-552670, dated Jun. 20, 2023, 5 page(s).
International Preliminary Report on Patentability, WIPO Application No. PCT/EP2021/054900, dated Jul. 4, 2022.
Office Action of JP Patent Application No. 2022-552670, dated Oct. 24, 2023, 11 page(s).
Office Action of JP Patent Application No. 2022-552647, dated Oct. 10, 2023, 7 page(s).
Restriction Requirement of U.S. Appl. No. 17/909,265, mailed Jan. 30, 2024, 8 page(s).

* cited by examiner

HEAD-MOUNTED VISUALIZATION UNIT AND VISUALIZATION SYSTEM COMPRISING LIGHT-TRANSMISSIVE OPTICAL SYSTEM

CROSS-REFERENCE TO RELATED APPLICATIONS

The present application is a national phase entry of International Application No. PCT/EP2021/055034, filed Mar. 1, 2021, which claims priority to German Patent Application No. 10 2020 202 624.6, filed Mar. 2, 2020, and German Patent Application No. 10 2020 131 029.3, filed Nov. 24, 2020, which are each incorporated herein by reference in their entirety.

The present invention relates to a head-mounted visualization unit and to a visualization system which comprises such a head-mounted visualization unit.

In microsurgery, surgical microscopes are used, with which the physician can observe the operating region, which is also referred to as the surgical site (OP site), with higher magnification. In addition to the magnification, the stereoscopic impression of the OP site is of critical importance for the success of the surgical procedure. Analog surgical microscopes with stereo optics and observation through eyepieces are regularly used in microsurgery.

Modern surgical microscopes sometimes offer the possibility of digital three-dimensional image capturing of the OP site as an alternative or in addition. The three-dimensional image data obtained can then be displayed on a screen, in particular a 3D monitor, or a head-mounted display (HMD). An HMD suitable for use in an operating environment can also be referred to as a surgical head-mounted display.

In a 3D monitor, for example, a first image with a first polarization can be displayed and a second image with a second polarization can be displayed at the same time, wherein the first polarization is substantially orthogonal to the second polarization. When using a head-mounted visualization unit, which transmits only light of the first polarization to a first eye and only light of the second polarization to the second eye, the viewer of the 3D monitor has a stereoscopic image impression.

Furthermore, there is often a desire to optically provide the operating physician with additional information, which they can also perceive when looking away from the screen. For this purpose, DE 10 2017 123894 B3, for example, proposes a head-mounted visualization unit, in particular an (HMD), which comprises a pane and a device for generating an image on the pane.

When using an HMD to display the three-dimensional image data, different images can be superimposed into the two beam paths that lead to the respective eye of the user, so that a stereoscopic image impression can be generated in this way. For example, US 2019/0339528 A1 discloses an HMD in the form of an augmented reality HMD (AR HMD), which is also referred to as a mixed reality display. An AR HMD is understood to be an HMD in which the user can see both superimposed image data and the natural environment. Partial regions of the natural field of view of the user of the HMD are darkened in a targeted manner before the images can be superimposed into the beam path for the respective eye in order to increase the visibility of the superimposed images in bright environments.

It has been shown that 3D monitors are preferred for presenting the three-dimensional image data due to the higher resolution and lower latency times compared to the display of the three-dimensional image data. At the same time, however, there is a desire to darken partial regions of the users natural field of view of the head-mounted visualization unit in order to block out interfering light sources or to increase the visibility of additional information that is superimposed.

Proceeding from this, the object of the present invention consists in specifying an improved head-mounted visualization unit and an improved visualization system.

This object was achieved with the subject matter of the main claim and the coordinate claim. Advantageous refinements for achieving the object are specified in the dependent claims.

A head-mounted visualization unit with an at least partially light-transmissive optical system is proposed. The optical system has a first optical channel, which is assigned to a first eye of a user of the head-mounted visualization unit, and a second optical channel, which is assigned to a second eye of the user. The first optical channel is substantially transmissive to optical radiation of a first polarization and substantially opaque to optical radiation of a second polarization, with the first polarization being substantially orthogonal to the second polarization. The second optical channel is substantially transmissive to optical radiation of the second polarization and substantially opaque to optical radiation of the first polarization. A polarizer and a light attenuator are arranged at least in the first optical channel. The light attenuator is arranged here downstream of the polarizer in a direction toward the first eye of the user.

The transmissivity for different polarizations can enable the user of the head-mounted visualization unit to perceive images with the corresponding polarization either with the left eye or with the right eye, so that a stereoscopic impression can be obtained. The orthogonal polarizations can be linear polarizations, for example a horizontal and a vertical polarization, or circular polarizations, for example a left-circular and a right-circular polarization. The arrangement of the light attenuator downstream of the polarizer makes it possible to block out parts of the natural field of view without influencing the channel separation required for stereoscopic perception.

The head-mounted visualization unit can be suitable in particular for use during a surgical procedure. In this context, the head-mounted visualization unit can also be referred to as a surgical HMD. In particular, the head-mounted visualization unit can be designed in such a way that it can be easily disinfected after a surgical procedure. Furthermore, the proposed head-mounted visualization unit can be made more lightweight due to the elimination of the need to generate the stereoscopic images in the head-mounted visualization unit itself. The head-mounted visualization unit can therefore have a lower energy consumption than known head-mounted visualization units, and longer use during the operation or a more lightweight head-mounted visualization unit can thus be provided with the same battery capacity.

In one exemplary embodiment, the polarizer has a linear polarization filter. For example, the polarization filter can be set up to only transmit light with vertical polarization.

According to another configuration, the polarizer comprises a λ/4 plate, wherein the λ/4 plate is arranged upstream of the linear polarization filter in the direction toward the first eye of the user. Depending on the orientation of the fast axis of the λ/4 plate in relation to the alignment of the subsequent linear polarization filter, the polarizer can be aligned to transmit light with a left-circular polarization or with a right-circular polarization, wherein light downstream of the linear polarization filter has a linear polarization.

The light attenuator can have a controllable liquid crystal layer. The liquid crystal layer can comprise one or more controllable liquid crystal pixels. In this way, it can be made possible to influence different points of the liquid crystal layer in their effect on incident light.

The light attenuator may have an output linear polarization filter and an input linear polarization filter. In exemplary embodiments, the input polarization filter of the light attenuator can be identical to the linear polarization filter of the polarizer. In this way, optical elements of the optical system can be omitted, if necessary. This can make it possible for the head-mounted visualization unit to be made more lightweight and possibly to be produced more cost-effectively.

The liquid crystal layer can be set up to superimpose additional information into the first channel. For example, liquid crystal pixels can be controlled differently in order to display additional parameters to the user of the head-mounted visualization unit.

In configurations of the head-mounted visualization unit, a display device is provided, with which additional information can be displayed in the first channel.

The head-mounted visualization unit can comprise a mirror for superimposing the additional information displayed by the display device into the first channel, wherein the mirror is arranged downstream of the light attenuator in the direction toward the first eye of the user.

It is also conceivable to provide a waveguide in order to superimpose the additional information displayed by the display device into the first channel, wherein the waveguide is arranged downstream of the light attenuator in the direction toward the first eye of the user. As a result, the light attenuator can make it easier to perceive the displayed additional information especially in a very bright environment.

A visualization system with a head-mounted visualization unit as described above and with a screen is furthermore proposed, wherein the screen is set up to present a first image with the first polarization and a second image with the second polarization for stereoscopically reproducing a sample image. For example, a screen which emits light line by line with a different polarization can be used.

In one configuration, the visualization system has a surgical microscope or endoscope, wherein the surgical microscope or endoscope has an image recording device for stereoscopically recording the sample image.

Aspects of the invention will now be explained in greater detail with reference to the drawing, in which.

Figure 1:
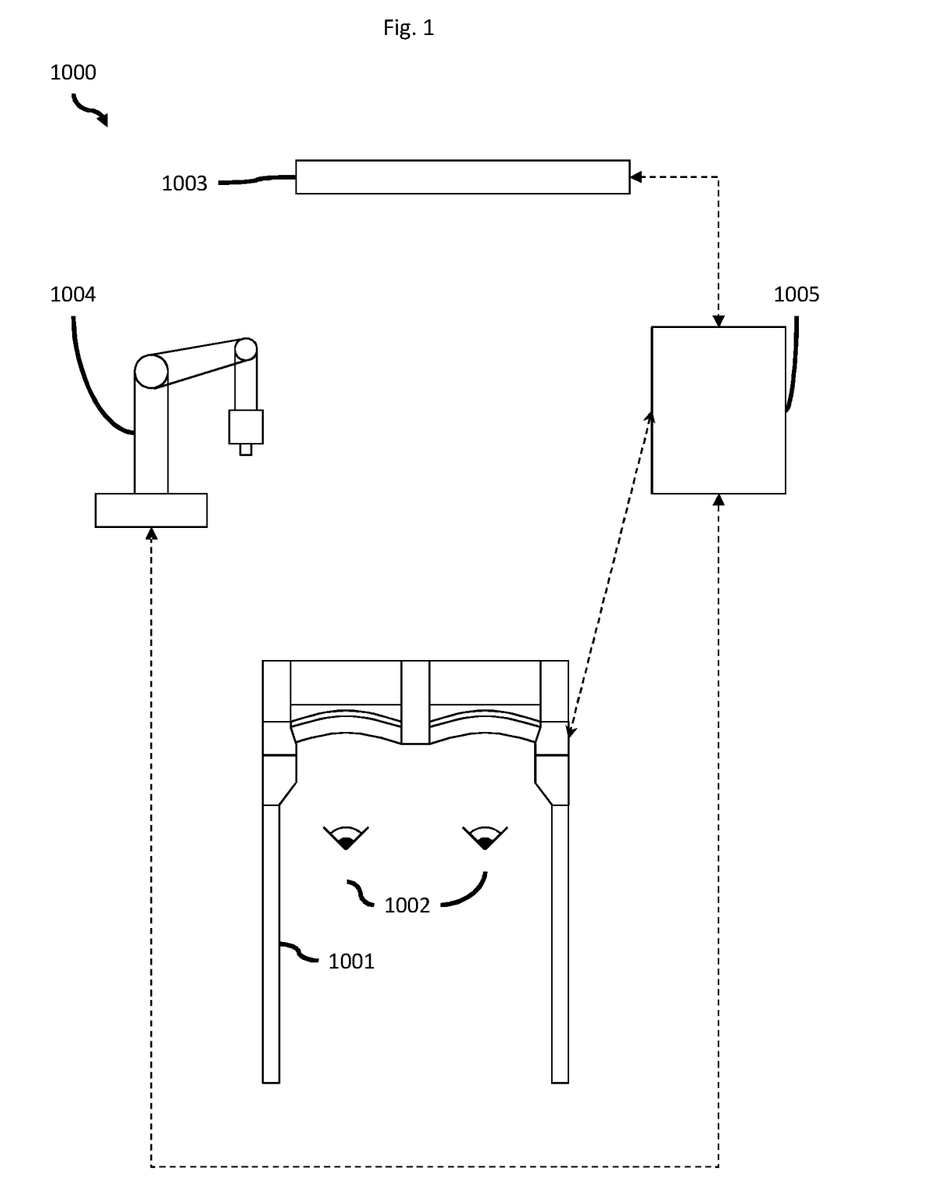
FIG. 1 shows a visualization system.

FIG. 1 shows a visualization system 1000, which comprises a surgical microscope 1004, with which three-dimensional image data of an OP site (not shown here) can be recorded. The surgical microscope 1004 is connected to a control device 1005. The control device 1005 can receive three-dimensional image data from the surgical microscope 1004 and display it on a 3D monitor 1003, for example. A surgeon 1002 can stereoscopically perceive the images displayed on the 3D monitor 1003 with the aid of a head-mounted visualization unit 1001. The head-mounted visualization unit can be set up to exchange additional information with the control device 1005. If necessary, this additional information can additionally be displayed to the surgeon 1002.

Figure 2:
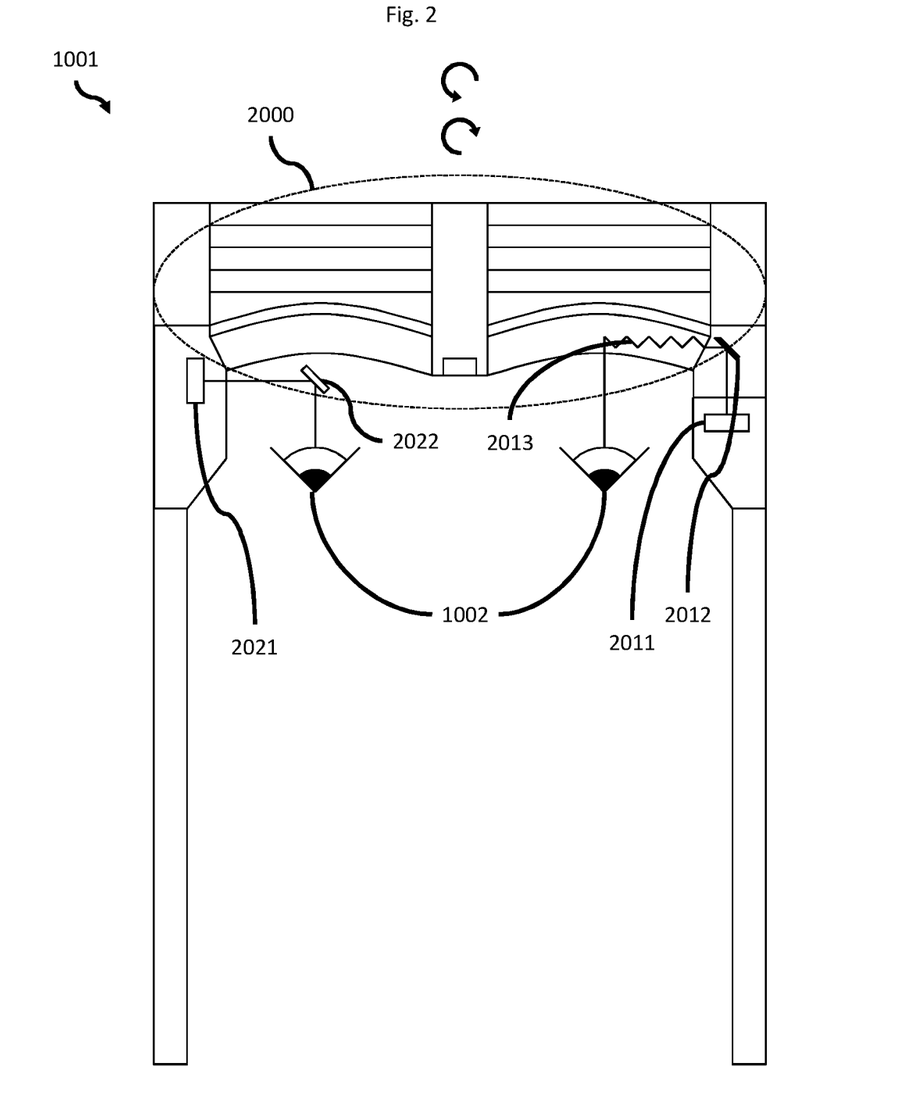
FIG. 2 shows a head-mounted visualization unit.

FIG. 2 shows further details of the visualization unit 1001 as an example. In particular, the visualization unit 1001 can have a partially light-transmissive optical system 2000. A first channel can be assigned to a first eye of a user 1002 of the head-mounted visualization unit, and a second channel can be assigned to the other eye of the user 1002.

FIG. 2 shows two variants by way of example, with which additional information can be superimposed into the respective channels. For example, it is conceivable to superimpose images from a display device 2021 into one channel via a partially transmissive mirror 2022. However, it may also be possible to superimpose additional information into the optical channel using a display device 2011, a mirror 2012, and a waveguide 2013.

Figure 3:
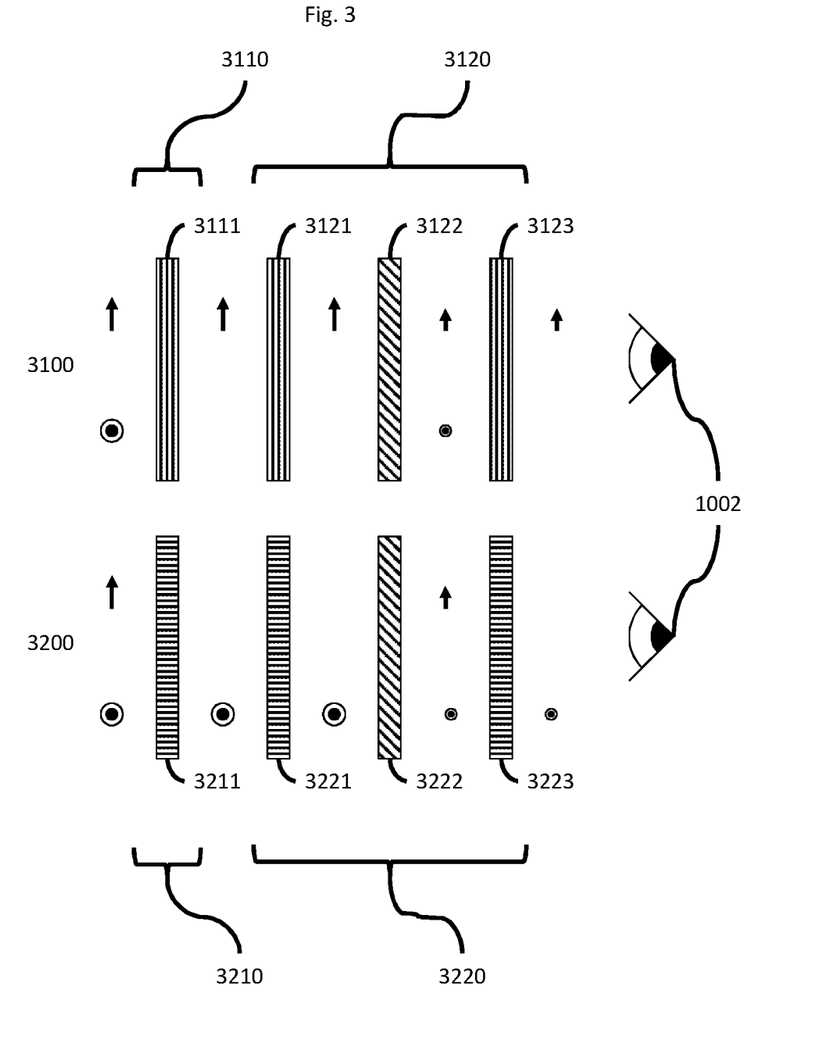
FIG. 3 shows an optical system.

FIG. 3 shows elements of a head-mounted visualization unit at a higher degree of detail. The head-mounted visualization unit has a first optical channel 3100, which is assigned to a first eye of a user 1002, and a second optical channel 3200, which is assigned to a second eye of the user 1002. The screen 1003 can present images with a first polarization and a second polarization. The first polarization can be, for example, a vertical polarization, as is indicated in FIG. 3 with an arrow pointing up, and a horizontal polarization, as is indicated in FIG. 3 with circles. The head-mounted visualization unit has a polarizer 3110 in the first optical channel 3100 and a light attenuator 3120 between the polarizer 3110 and the eye of the user 1002. The polarizer 3110 comprises a linear polarization filter 3111, which allows only vertically polarized light to pass. The light attenuator 3120 has an input polarization filter 3121 and an output polarization filter 3123. A liquid crystal layer 3122, which has a plurality of individually controllable liquid crystal pixels (not shown), is arranged between the input polarization filter 3121 and the output polarization filter 3123. The liquid crystal layer 3122 brings about a rotation of the vertical polarization, with the result that a linear combination of a vertical and a horizontal polarization is present downstream of the liquid crystal layer. In this case, the degree of rotation can be changed by appropriately controlling the liquid crystal layer 3122. The output polarization filter 3123 ensures that only light with vertical polarization is transmitted. Accordingly, the liquid crystal layer 3122 in combination with the input polarization filter 3121 and the output polarization filter 3123 causes light attenuation.

Similarly, the second optical channel 3200 comprises a polarizer 3210 with a linear polarization filter 3211 and a light attenuator 3220 with an input polarization filter 3221, a liquid crystal layer 3222, and an output polarization filter 3223. In contrast to the first channel 3100, the second channel 3200 is transmissive only to light with horizontal polarization. Thus, a channel separation takes place that allows the user of the head-mounted visualization unit to stereoscopically perceive the images displayed by the screen 1003.

Figure 4:
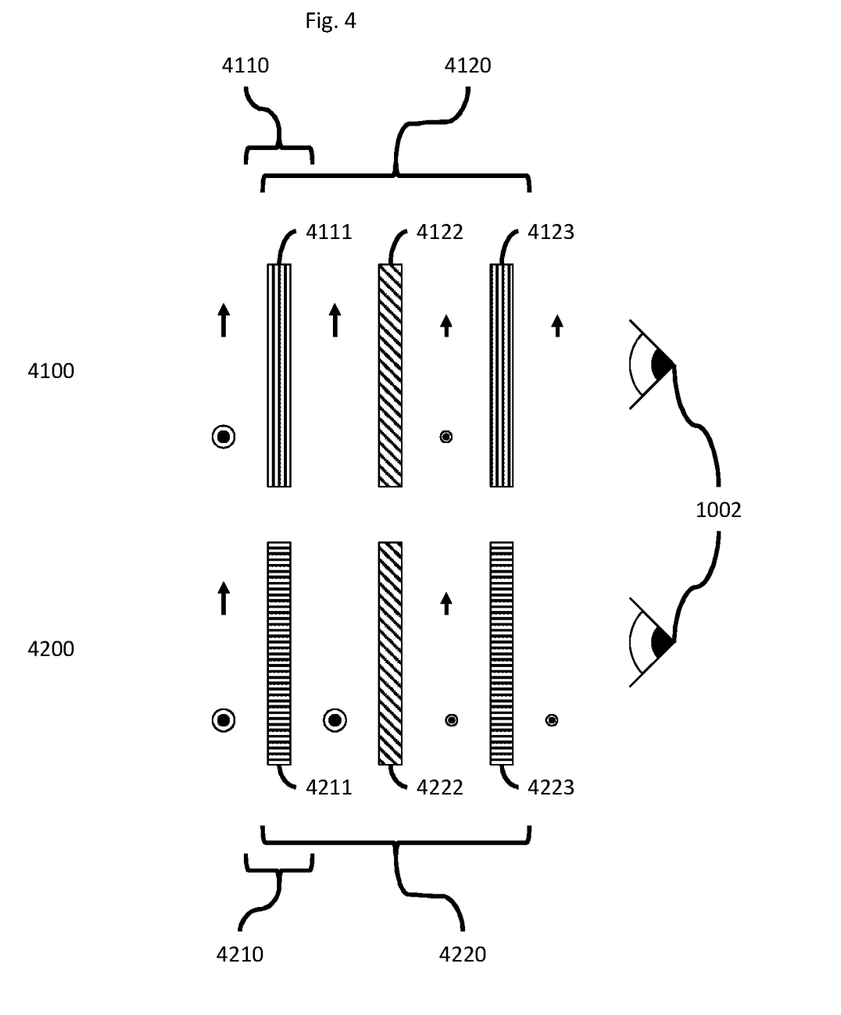
FIG. 4 shows an optical system.

FIG. 4 shows a further, partially light-transmissive optical system with a first channel 4100 and a second channel 4200. The first channel has a polarizer 4110 and a light attenuator 4120 arranged thereafter. The linear polarization filter 4111 of the polarizer 4110 is thus identical to an input polarization filter of the light attenuator 4120. The light attenuator 4120 further has a liquid crystal layer 4122 and an output polarization filter 4123.

The channel 4100 is in turn substantially transmissive to light with vertical polarization. The optical system further has a second channel 4200 with a polarizer 4210 and a light attenuator 4220. The linear polarization filter 4211 of the polarizer 4210 is in turn identical to the input polarization filter of the light attenuator 4220. The light attenuator 4220 additionally has a liquid crystal layer 4222 and an output polarization filter 4223. In contrast to the first channel 4100, the second channel 4200 is transmissive substantially only to light with horizontal polarization.

The optical system of FIG. 4 makes it possible to eliminate a linear polarization filter both in the first and in the second channel compared to the optical system of FIG. 3.

Figure 5:
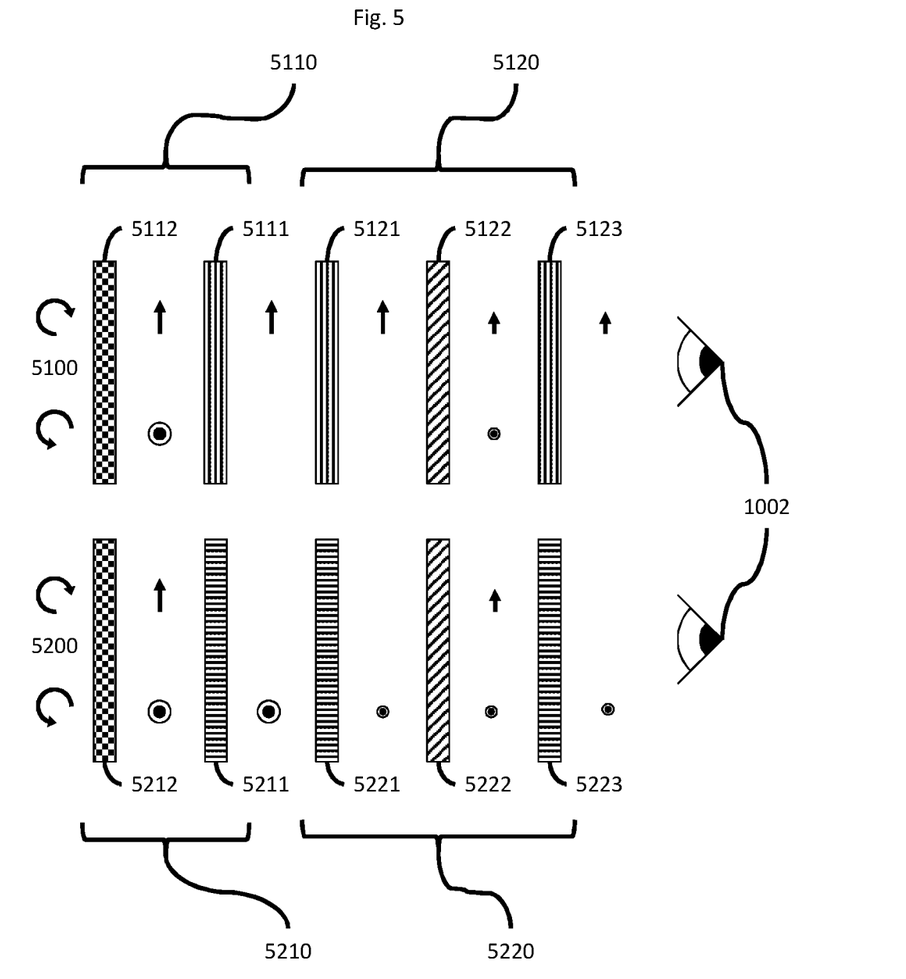
FIG. 5 shows an optical system.

FIG. 5 shows a further optical system which is suitable for 3D monitors which generate images with left-circular polarization and right-circular polarization. The use of circular polarizations offers the advantage for the user of the head-mounted visualization unit that a clean separation of the images assigned in each case to the left and right channel remains possible even when the head is tilted.

The optical system according to FIG. 5 has a first channel 5100 and a second channel 5200. A polarizer 5110 and a light attenuator 5120 are arranged in the first channel 5100. The polarizer comprises a linear polarization filter 5111 and a $\lambda/4$ plate 5112. The linear polarization filter 5111 is arranged between the $\lambda/4$ plate 5112 and the eye of the user 1002 of the head-mounted visualization unit. The polarizer 5110 transmits only light with right-circular polarization, which means that there is vertically polarized light downstream of the polarizer 5110. With the aid of the input polarizer 5121, the liquid crystal layer 5122, and the output polarization filter 5123, the light arriving before the light attenuator 5120 is attenuated.

Similarly, the second channel 5200 has a polarizer 5210 and a light attenuator 5220. The polarizer 5210 comprises a $\lambda/4$ plate 5212 and has a linear polarization filter 5211 arranged between the $\lambda/4$ plate 5212 and the eye of the user 1002 of the head-mounted visualization unit. The polarizer 5210 has the effect that only left-circular light can pass through the polarizer 5210 and is present as horizontally polarized light downstream of the polarizer 5210. The horizontally polarized light is then attenuated by means of the input polarization filter 5221, the liquid crystal layer 5222, and the output polarization filter 5223.

Figure 6:
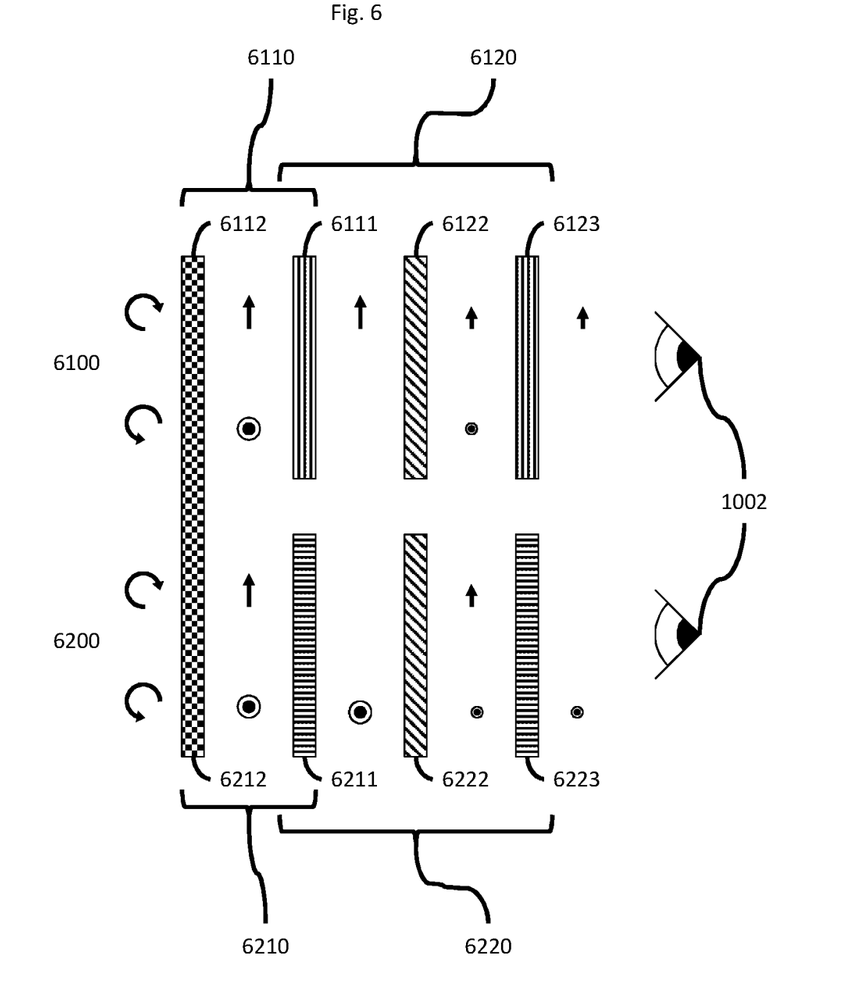
FIG. 6 shows an optical system.

FIG. 6 shows a further example of a head-mounted visualization unit, which can be used with circular polarization. The optical system of the head-mounted visualization unit again has a first channel 6100 and a second channel 6200.

The polarizer 6110 of the first channel 6100 and the polarizer 6210 of the second channel 6200 share the same $\lambda/4$ plate 6112/6212. Furthermore, the input polarization filter of the light attenuator 6120 is identical to the linear polarization filter 6111 of the polarizer 6110, and the input polarization filter 6211 of the light attenuator 6220 is identical to the linear polarization filter 6211 of the polarizer 6210. Due to the different alignments of the light attenuators 6120 and 6220 in relation to the fast axis of the $\lambda/4$ plate 6112/6212, only right-circular light is allowed through in the first channel 6100 and only left-circular light is allowed through in the second channel 6200.

Figure 7:
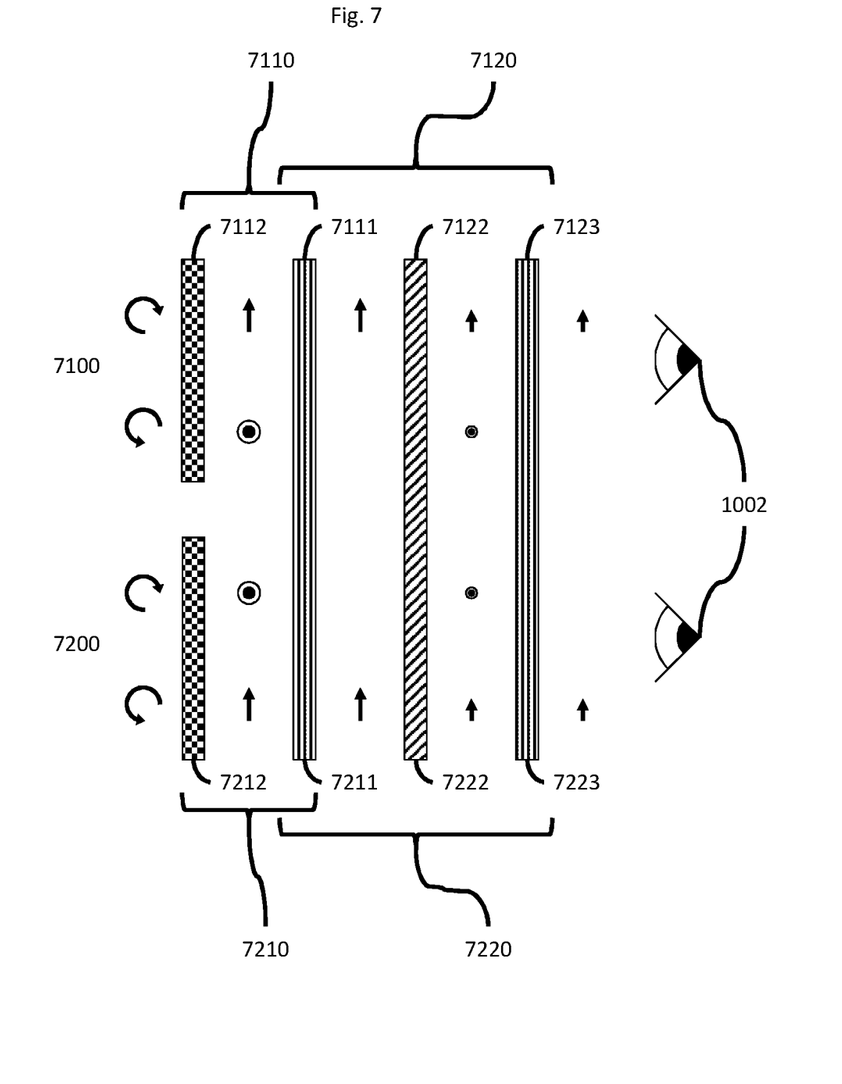
FIG. 7 shows an optical system.

FIG. 7 shows further details of a head-mounted visualization unit.

Similar to the way in which the input polarization filter of the light attenuator 4120 is identical to the linear polarization filter 4111 of the polarizer 4110 in FIG. 4, in the exemplary embodiment according to FIG. 7, the input polarization filter 7111 of the light attenuator 7120 is identical to the linear polarization filter of the polarizer 7110 and the input polarization filter of the light attenuator 7220 is identical to the linear polarization filter 7211 of the polarizer 7210. The light attenuator 7120 of the first channel 7100 is identical to the light attenuator 7220 of the second channel. Due to different alignments of the $\lambda/4$ plates 7112 and 7212 in relation to the linear polarization filter 7111/7211, light in the first channel 7100 that is incident with right-circular polarization on the $\lambda/4$ plate 7112 is allowed through in the first channel 7100, and light that is incident with left-circular polarization on the $\lambda/4$ plate 7212 is allowed through in the second channel 7200. Accordingly, the optical system according to FIG. 7 also allows channel separation, as a result of which the user of the head-mounted visualization unit can stereoscopically perceive the three-dimensional image data displayed by a screen.

The invention claimed is:

1. A visualization system for observing a surgical site (OP site) in an operating environment
    having a head-mounted visualization unit,
    having an at least partially light-transmissive optical system,
    wherein the optical system has a first optical channel, which is assigned to a first eye of a user of the head-mounted visualization unit, and a second optical channel, which is assigned to a second eye of the user,
    wherein the first optical channel is substantially transmissive to optical radiation of a first polarization and substantially opaque to optical radiation of a second polarization, with the first polarization being substantially orthogonal to the second polarization,
    wherein the second optical channel is substantially transmissive to optical radiation of the second polarization and substantially opaque to optical radiation of the first polarization,
    wherein a polarizer and a light attenuator are arranged at least in the first optical channel, and
    wherein the light attenuator is arranged downstream of the polarizer in a direction toward the first eye of the user, and
    having a screen, wherein the screen is set up to present a first image of the OP site with the first polarization and a second image of the OP site with the second polarization for stereoscopically reproducing a sample image.

2. The visualization system for observing an OP site in an operating environment as claimed in claim 1,
    wherein the polarizer comprises a linear polarization filter.

3. The visualization system (1000) for observing an OP site in an operating environment as claimed in claim 2,
    wherein the polarizer comprises a $\lambda/4$ plate,
    wherein the $\lambda/4$ plate is arranged upstream of the linear polarization filter in the direction toward the first eye of the user.

4. The visualization system for observing an OP site in an operating environment as claimed in claim 1,
    wherein the light attenuator comprises a controllable liquid crystal layer.

5. The visualization system for observing an OP site in an operating environment as claimed in claim 4,
    wherein the liquid crystal layer comprises one or more individually controllable liquid crystal pixels.

6. The visualization system for observing an OP site in an operating environment as claimed in claim 1, wherein the light attenuator has a linear output polarization filter and
a linear input polarization filter.

7. The visualization system for observing an OP site in an operating environment as claimed in claim 6,
wherein the linear input polarization filter of the light attenuator is identical to the linear polarization filter of the polarizer.

8. The visualization system for observing an OP site in an operating environment as claimed in claim 5,
wherein the liquid crystal layer is set up to superimpose additional information into the first channel.

9. The visualization system for observing an OP site in an operating environment as claimed in claim 1,
wherein the head-mounted visualization unit has a display device for displaying additional information in the first channel.

10. The visualization system for observing an OP site in an operating environment as claimed in claim 9,
wherein a mirror is provided to superimpose the additional information displayed by the display device into the first channel,
wherein the mirror is arranged downstream of the light attenuator in the direction toward the first eye of the user.

11. The visualization system (1000) for observing an OP site in an operating environment as claimed in claim 9,
wherein a waveguide is provided to superimpose the additional information displayed by the display device into the first channel,
wherein the waveguide is arranged downstream of the light attenuator in the direction toward the first eye of the user.

12. The visualization system for observing an OP site in an operating environment as claimed in claim 1,
wherein the first polarization and the second polarization are circular polarizations.

13. The visualization system for observing an OP site in an operating environment as claimed in claim 1,
wherein the screen is set up to emit light line by line with different polarization.

14. The visualization system for observing an OP site in an operating environment as claimed in claim 1,
having a surgical microscope or endoscope,
wherein the surgical microscope or endoscope has an image recording device for stereoscopically recording the sample image.

* * * * *

UNITED STATES PATENT AND TRADEMARK OFFICE
CERTIFICATE OF CORRECTION

PATENT NO. : 11,953,687 B2
APPLICATION NO. : 17/909270
DATED : April 9, 2024
INVENTOR(S) : Christoph Hauger et al.

Page 1 of 1

It is certified that error appears in the above-identified patent and that said Letters Patent is hereby corrected as shown below:

In the Claims

In Column 6, Line 52, Claim 3, delete "(1000)".

In Column 8, Line 1, Claim 11, delete "(1000)".

Signed and Sealed this
Twenty-third Day of July, 2024

Katherine Kelly Vidal
*Director of the United States Patent and Trademark Office*